(12) United States Patent
Reingruber et al.

(10) Patent No.: US 11,231,394 B2
(45) Date of Patent: Jan. 25, 2022

(54) MEASURING DEVICE FOR ASCERTAINING A MEASURAND OF A MEASUREMENT GAS

(71) Applicant: AVL LIST GMBH, Graz (AT)

(72) Inventors: Herbert Reingruber, Graz (AT); Wolfgang Schindler, Graz (AT); Klaus-Christoph Harms, Thal/Graz (AT); Tristan Reinisch, Graz (AT)

(73) Assignee: AVL List GmbH, Graz (AT)

( * ) Notice: Subject to any disclaimer, the term of this patent is extended or adjusted under 35 U.S.C. 154(b) by 0 days.

(21) Appl. No.: 16/956,497

(22) PCT Filed: Dec. 28, 2018

(86) PCT No.: PCT/EP2018/097061
§ 371 (c)(1),
(2) Date: Jun. 19, 2020

(87) PCT Pub. No.: WO2019/129834
PCT Pub. Date: Jul. 4, 2019

(65) Prior Publication Data
US 2021/0096103 A1    Apr. 1, 2021

(30) Foreign Application Priority Data
Dec. 28, 2017   (AT) .............. A 51084/2017

(51) Int. Cl.
*G01N 29/036*   (2006.01)
*G01N 29/24*    (2006.01)
(Continued)

(52) U.S. Cl.
CPC ....... *G01N 29/036* (2013.01); *G01N 21/1702* (2013.01); *G01N 29/2425* (2013.01); *G01N 33/0036* (2013.01); *G01N 2021/1704* (2013.01)

(58) Field of Classification Search
CPC ............. G01N 29/036; G01N 29/2425; G01N 29/2418; G01N 21/1702; G01N 2021/1704; G01N 33/0036
See application file for complete search history.

(56) References Cited

U.S. PATENT DOCUMENTS

| | | | | |
|---|---|---|---|---|
| 4,506,381 | A | * | 3/1985 | Ono ........................ H03G 3/32 381/108 |
| 5,528,924 | A | * | 6/1996 | Wajid ................... G01N 29/036 73/24.06 |

(Continued)

FOREIGN PATENT DOCUMENTS

WO       2014032771 A1      3/2014

OTHER PUBLICATIONS

Brand C et al: "Pulsed-laser excitation of acoustic modes in open high-Q photoacoustic resonators for trace gas monitoring: results for C2H4", Applied Optics, Optical Society of America, Washington, DC; US, vol. 34, No. 18, Jun. 20, 1995 (Jun. 20, 1995), pp. 3257-3266, XP002486473, ISSN: 0003-6935, DOI: 10.1364/AO. 34.003257.

(Continued)

*Primary Examiner* — Suman K Nath
(74) *Attorney, Agent, or Firm* — Dykema Gossett PLLC

(57) ABSTRACT

Aspects of the present disclosure are directed to a measuring device for determining a measured variable of a measuring gas by means of a photoacoustic method. In some embodiments, the measuring device includes a flow channel for the measuring gas having at least one feed line, a photoacoustic measuring cell and a discharge line. in such an embodiment, the measuring device further includes at least one acoustic filter member tuned to a useful frequency of the measuring cell, and at least one cavity resonator arranged on the flow channel.

14 Claims, 7 Drawing Sheets

(51) Int. Cl.
*G01N 21/17* (2006.01)
*G01N 33/00* (2006.01)

(56) References Cited

U.S. PATENT DOCUMENTS

| | | |
|---|---|---|
| 7,345,766 B2 | 3/2008 | Schindler et al. |
| 2002/0194897 A1 | 12/2002 | Arnott et al. |
| 2016/0313233 A1* | 10/2016 | Zangmeister ...... G01N 21/1702 |

OTHER PUBLICATIONS

A. Miklós et al.: "Application of acoustic resonators in photoacoustic trace gas analysis and metrology"; Review of Scientific Instruments, American Institute of Physics, vol. 72, No. 4, Apr. 2001; doi.org/10.1063/1.1353198.

D.C.Dumitras et al.: "Ultrasensitive CO2 laser photoacoustic system"; Infrared Physics & Technology; Elsevier, vol. 53, Nr. 5, Sep. 2010, pp. 308-314 doi.org/10.1016/j.infrared.2010.05.001.

F. G. C. Bijnen et al.: "Geometrical optimization of a longitudinal resonant photoacoustic cell for sensitive and fast trace gas detection" Review of Scientific Instruments vol. 67, No. 2914 (1998); doi.org/10.1063/1.1147072.

* cited by examiner

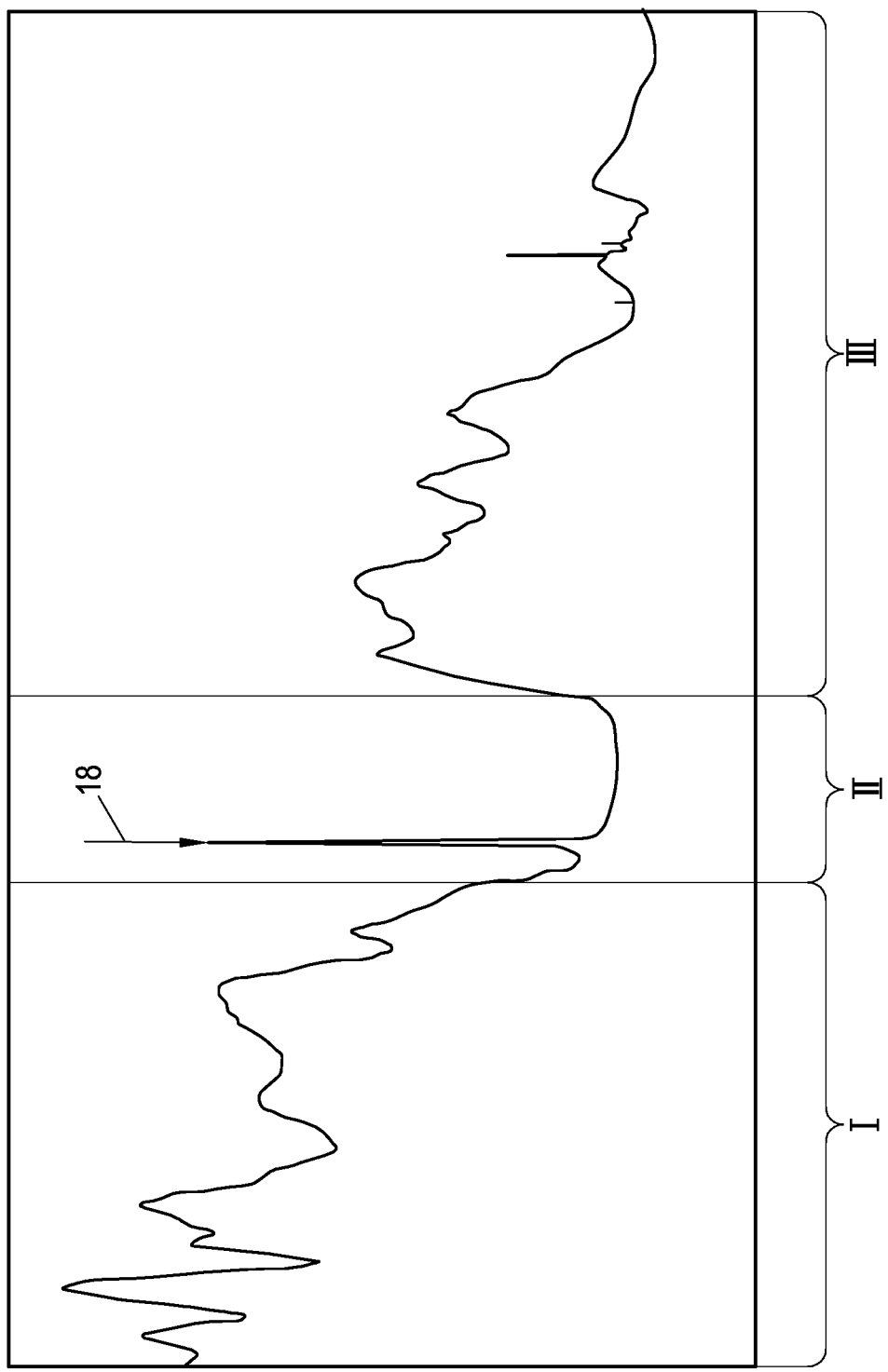

MEASURING DEVICE FOR ASCERTAINING A MEASURAND OF A MEASUREMENT GAS

CROSS-REFERENCE TO RELATED APPLICATIONS

This application is a national stage filing based upon International PCT Application No. PCT/EP2018/097061, filed 28 Dec. 2018, which claims the benefit of priority to Austria application No. A 51084/2017, filed 28 Dec. 2017.

BACKGROUND

The present invention relates to a measuring device for determining a measured variable of a measuring gas using a photoacoustic method, wherein the measuring device has a flow channel for the measuring gas having at least one feed line, a photoacoustic measuring cell and a discharge line.

Furthermore, the invention relates to a method for suppression of sound interferences in a measuring device for determining a measured variable of a measuring gas by means of a photoacoustic method, wherein the measuring gas is conducted via a flow channel which runs through at least one feed line, a photoacoustic measuring cell and a discharge line.

Photoacoustic spectroscopy (PAS) is used very successfully for measurement methods in many areas of gas and particle measurement technology. The measuring gas to be examined (aerosol) is excited to density or pressure oscillations in an acoustically resonant measuring cell by means of an intensity-modulated laser. This sound signal is received by a microphone and converted into an electrical signal. Corresponding systems are used, for example, for determining the mass concentration [mg/m] of soot particles in the exhaust gas of internal-combustion engines.

The acoustic frequency spectrum recorded by the microphone also includes unwanted interfering frequencies from various sources, e.g. flow noise of the inflowing measuring gas, engine noise or various ambient noises and vibrations (structure-borne sound). The sound can take the following paths in particular:

Via the feed/discharge lines to the measuring cell as airborne sound or as structure-borne sound, which is transmitted from the walls of the lines Via the surroundings of the measuring cell also as airborne sound or as structure-borne sound, which is transmitted, for example, via the mounting of the measuring cell For interference suppression, the structure-borne sound at the measuring cell mounting can be suppressed, for example, by the use of attenuators such as rubber buffers, the apparatus housing can be provided with double walls to shield airborne sound coming from the surroundings, and potential internal sources of interference of the apparatus (pumps, fans, etc.) can be stored accordingly (for example, via rubber buffers) or they can be installed in an external housing. Furthermore, the frequency response of the microphone and subsequent amplifier can be selected according to the useful frequency. The interference influences can also be specifically influenced by a suitable material selection.

Despite numerous measures already implemented, there is still a need for additional improvements for interference suppression. In particular, interferences that enter the PAS measuring cell via the airborne sound path via the feed or discharge line represent a major problem. The higher the extraction flow is chosen (which contributes to the improvement of dynamics), the higher the flow noise.

The present invention has the object to effectively suppress interference noises even at high flow velocities and to increase the measuring accuracy and reliability of the measuring device.

SUMMARY OF THE INVENTION

These and further objects are solved by a measuring device of the type mentioned above according to the invention in that the measuring device has at least one acoustic filter member tuned to the useful frequency of the measuring cell, which comprises at least one cavity resonator arranged on the flow channel. Preferably, the interior of the cavity resonator is in connection with the interior of the flow channel. The acoustic filter member effectively eliminates interference frequencies in the range of the useful frequency. The preferred cavity resonators are cavity resonators open on one side towards the flow channel. The desired properties of the acoustic filter can be specifically influenced to one another via the shape, size and, if appropriate, the relative arrangement of individual cavity resonators.

In the context of the present disclosure, "useful frequency" is the frequency that is evaluated for determining the measurement property. In general, this is a resonant frequency of the measuring cell and in general, the useful frequency coincides with the excitation frequency of the laser of the measuring cell. If necessary, a measuring cell can also be operated with different useful frequencies. In measuring devices for determining the mass concentration of soot particles in the exhaust gas of internal-combustion engines, for example, a useful frequency in the range of about 1000 to 12000 Hz has proven to be advantageous, although other frequency ranges can also be used reasonably depending on the respective application.

Advantageously, the axis of the cavity resonator is aligned normally to the axis of the flow channel. This enables a simple construction of the cavity resonator, the acoustic properties of which can be easily determined.

Advantageously, at least one cavity resonator is formed as a double-sided cavity resonator having a first and a second neck portion, wherein the first neck portion is preferably arranged opposite to the second neck portion. This allows the value peaks of the negative sound pressure amplification to be widened in the sound pressure course.

In another advantageous embodiment, the acoustic filter member has a plurality of cavity resonators which enter consecutively into the flow channel. This allows several negative value peaks to be realized at different frequencies in the sound pressure course. The exact position of the value peaks in the frequency course depends essentially on the length of the resonator necks. The consequences that a certain shape of a cavity resonator or a certain arrangement of cavity resonators have on the sound pressure course can be determined by appropriate routine tests. The person skilled in the art is thus able to create suitable acoustic filter members for a given measuring device, provided that he is aware of the teachings of the present disclosure.

Advantageously, at least one acoustic filter member is designed for negative sound pressure amplification in a first frequency range which comprises the fundamental frequency of the useful frequency. In this way, the interference noise is specifically reduced in the frequency field in which the respective measuring cell operates.

In another advantageous embodiment, at least one acoustic filter member is designed for negative sound pressure amplification in at least one second frequency range which comprises a multiple of the fundamental frequency of the useful frequency. By combining a plurality of cavity resonators, one or more frequency ranges can thus be effectively attenuated and suppressed.

In a preferred embodiment, at least one cavity resonator is formed to be cylindrical. A cylindrical cavity resonator is easy to manufacture and can also be easily cleaned. Furthermore, high accuracy can be achieved for the design of the acoustic filter members with relatively simple calculation and simulation models.

Advantageously, at least two cavity resonators are formed cylindrically and have a different length and/or diameter. By the use of several cavity resonators having slightly varying lengths, for example, it is possible to achieve wider but not as deep indentations or negative value peaks in the sound pressure course.

Another advantageous embodiment provides that the length of at least one cavity resonator is adjustable. This allows the properties of the acoustic filter member to be adapted, for example, to changed ambient conditions (e.g. a different pressure, temperature or measuring gas). The length adjustment can be realized in a simple way, for example, by means of appropriate screw connections.

In another advantageous embodiment, the measuring cell is arranged in an airtight housing. Airtight here means that the housing is essentially pressure-tight achieved and can be brought to negative pressure and/or vacuum. For example, a vacuum pump can be provided on the measuring device with which the housing can be evacuated. This attenuates the airborne sound affecting the measuring cell and reduces the interference noise transmitted in this way. According to the technical definition, negative pressure is defined as a pressure level below normal pressure; a pressure level below 300 hPa is referred to as rough vacuum.

In another aspect, the method for solving the problem mentioned at the beginning provides, according to the invention, that at least one acoustic filter member is provided in the flow channel, which is adjusted to a negative sound pressure amplification in a first frequency range, which comprises the fundamental frequency of the useful frequency.

Advantageously, at least one acoustic filter member is provided in the flow channel, which is adjusted to a negative sound pressure amplification in at least one second frequency range, which comprises a multiple of the basic frequency of the useful frequency.

In another advantageous embodiment, the adjusting of the at least one acoustic filter comprises a constructive defining and/or adjusting of at least one or a plurality of the following features of a cavity resonator: Shape, position, length, diameter, length of a cylindrical cavity resonator, diameter of a cylindrical cavity resonator. This allows acoustic filter members to be created in a targeted manner by the use of cavity resonators having known properties, such as Helmholz resonators or similar. This also allows a constructive and computationally simple implementation of the acoustic filter members used in the method.

A further preferred embodiment of the method according to the invention provides that a negative pressure and/or vacuum is generated in a housing which can be brought to negative pressure and/or vacuum and in which the measuring cell is arranged.

BRIEF DESCRIPTION OF THE DRAWINGS

The present invention is explained in more detail below with reference to FIGS. 1 to 10, which show exemplary, schematic and non-restrictive advantageous embodiments of the invention. In the drawings:

FIG. 2 is an exemplary frequency spectrum of a sound signal recorded in a measuring cell.

DETAILED DESCRIPTION

Figure 1:
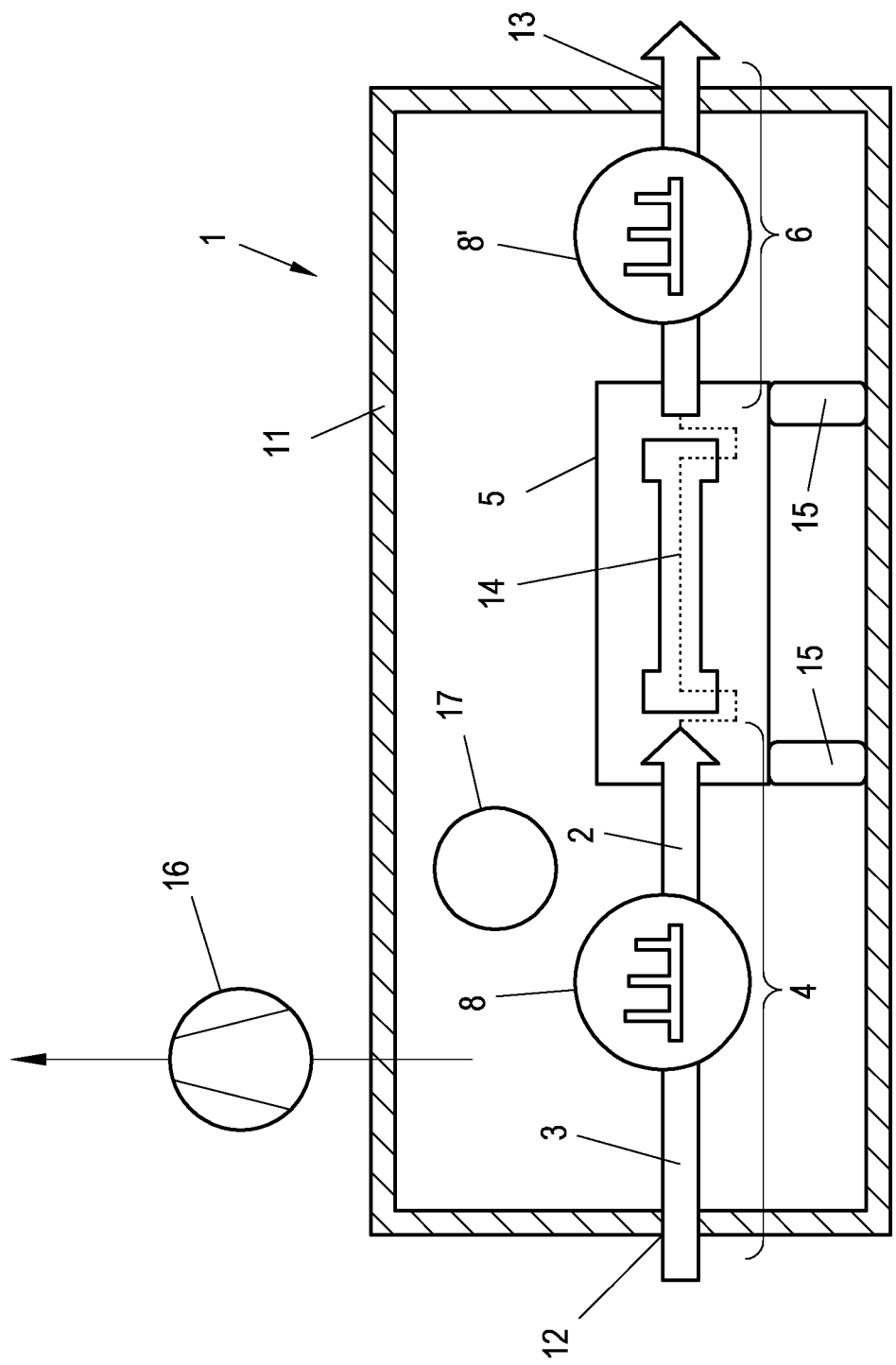
FIG. 1 is a schematic representation of a measuring device according to the invention.

The basic members of a measuring device 1 are represented schematically in FIG. 1. The essential components of measuring device 1 are protectively arranged in a housing 11, wherein a measuring gas 2 is fed to measuring device 1 at a measuring gas inlet 12 and the measuring gas 2 leaves measuring device 1 after measurement at a measuring gas outlet 13. The path of the measuring gas 2 inside the measuring device 1 is defined by a flow channel 3, which runs from the measuring gas inlet 12 to the measuring gas outlet. The flow channel 3 leads the measuring gas 2 over a photoacoustic measuring cell 5, in which the measuring gas is excited in a known manner with pulsed or modulated laser radiation.

The flow channel 3 can thus be divided into three portions: a feed line 4 from the measuring gas inlet 12 to the measuring cell 5, a flow path 14 which leads through the measuring cell and whose course is defined by it, and a discharge line 6 which runs from the measuring cell 5 to the measuring gas outlet 13.

To reduce the transmission of structure-borne sound from the housing 11 to the measuring cell 5, the measuring cell 5 is mounted on attenuators 15 (e.g. rubber buffers).

The attenuators 15 attenuate vibrations and ambient noise that affect the housing 11 from outside. In order to also reduce the airborne sound impacting the measuring cell 5, a vacuum can be created in the interior of the housing 11 using a vacuum pump 16. The higher the quality of the vacuum, the more effectively airborne sound can be suppressed.

Alternatively or additionally, additional acoustic members may be provided in the interior, such as a Helmholz resonator 17 (possibly a plurality of them), with which a reduction of the noise level in a defined frequency range can be achieved. The Helmholz resonator(s) 17 is (are) preferably tuned so that interference frequencies at and near the useful frequency(ies) of the photoacoustic measurement cell 5 are absorbed.

In order to reduce sound transmission in the structure-borne sound path via the line members of flow channel 3, this channel can have flexible hoses (e.g. made of Viton® Tygon®, silicone or similar materials), at least in portions. A transmission of acoustic interference to the structure-borne sound path in the used, thus audible acoustic frequency range (<10 kHz) can be largely excluded.

Only interferences that reach the measuring cell 5 by the airborne sound path via feed line 4 and discharge line 6 can hardly be effectively eliminated with the measures described above and therefore represent a major problem. These interferences are often broadband interferences which partly also contain the useful frequency(ies) and thus contribute to the measured value noise. The sources of these interferences are the engine noise itself (transmitted by the exhaust and extraction system) and, above all, the flow noise. This occurs on all edges, cross-sectional changes, flow obstacles, etc., i.e. mainly on components such as valves, splitters, frames or filters. The higher the extraction flow, the greater the flow noise. However, in order to increase the dynamics of the measurement, it is desirable to increase the extraction flow, which also increases the flow velocity in flow channel 3.

Particularly in the case of mobile measuring apparatuses, the interference sound that is transmitted through the hoses is problematic due to the compact structure and the lower weight. Particularly with a large flow (e.g. more than 6 L/min) through the measuring chamber 5, the interference sound is very noticeable.

In this context, it must also be taken into account that the acoustic properties of the flow channel (both in feed line 4, as well as in measuring cell 5 and in discharge line 6) cannot be changed arbitrarily, as possible negative effects must also be taken into account. In order to be able to take into account the gas exchange times (rise time/fall time) of an internal-combustion engine in the measurement result, for example, the slimmest possible shape of the flow channel 3 is preferred, which is as constant as possible, especially in the area of the feed line 4 and/or the discharge line 6, and in particular free of buffer volume or extensions of the flow channel 3. In other words, the flow channel 3 has a constant cross-section in the area of the feed line 4 and/or the discharge line 6 and is free of buffer volume. In particular, "area" here means a portion that corresponds to a certain multiple of the cross-section of flow channel 3. With regard to feed line 4, for example, this would be at least three times the cross-section of the flow channel 3 at measuring gas inlet 12; with regard to discharge line 6, for example, at least three times the cross-section of flow channel 3 at measuring gas outlet 13. In particular, impermissible cross-sectional changes in the feed line 4 (and, if necessary, also in the discharge line 6) must be avoided. A cross-sectional change can be regarded as "impermissible" in particular if it changes the temporal course of the volume flow in the area of the measuring cell 5 compared to the course originally prevailing at the measuring input 12 to such an extent that at certain points in time the permissible measuring tolerance would be exceeded or undercut.

In order to minimize the consequences of the flows reaching the measuring cell 5 on the airborne sound path via the flow channel 3, an acoustic filter member 8 is provided in the feed line 4, which is designed for a negative sound pressure amplification in at least one frequency range tuned to the useful frequency. The acoustic filter member 8 comprises at least one, preferably a plurality of cavity resonators 7 arranged at the flow channel 3, the preferred embodiments of which are exemplary described below. The design of the cavity resonator or cavity resonators is selected in such a way that, as a whole, they represent an acoustic band-stop or notch filter. The properties of the acoustic filter member defined by the cavity resonator(s) 7 can be tuned by variation of the shape and dimensions of the cavity resonators 7, in particular their lengths l and diameter d.

Alternatively or additionally, a second acoustic filter member 8' can be arranged in the area of the discharge 6 in flow channel 3. The second acoustic filter member 8' can be identical to the first acoustic filter member 8 in terms of its dimensions and properties, but it can also be designed differently if, for example, this appears reasonable due to different dimensions or line diameters.

The desired behavior of the acoustic filter member 8 (and the second acoustic filter member 8') is described below in the context of FIG. 2. FIG. 2 shows a frequency spectrum of a sound signal recorded by a measuring cell 5. The measuring cell 5 is excited with a useful frequency 18, wherein the intensity of the signal at this useful frequency 18 is evaluated for determining the measured variable of the measuring gas 2. The frequency spectrum can essentially be divided into three band areas, a lower band area I of frequencies up to 3900 Hz, a middle band area ii of frequencies between 3900 Hz and 5100 Hz, and an upper band area III of frequencies above 5100 Hz. The middle band area II comprises the useful frequency 18, which in this example is approx. 4100 Hz.

To reduce the disturbing influence of noise in the middle band area II, a band-stop filter is used as acoustic filter member 8, which attenuates the frequencies in the middle band area II, as can be clearly seen from the course of the frequency line.

The preferred acoustic filter member 8, 8' is a relatively simple arrangement of cylindrical cavity resonators 7, which enter into the flow channel 3 transversely to the flow direction.

The applicants for the present invention have examined the impact of such cylindrical cavity resonators 7 on the frequency-related sound pressure level. The aim was to adapt an acoustic filter member 8 so that the noise level is attenuated in the relevant measuring area around the useful frequency 18 and is as low as possible at high and low flow rates. In this context, 3D simulations were performed with the simulation software COMSOL to better understand the basic behavior of such acoustic filter members 8 and to develop methods for the design of such acoustic filter members 8.

FIGS. 3 to 12 show the simulation results, each having a representation of the acoustic filter member used and the sound pressure distribution calculated therewith.

The simulation series was performed using several models, each defining a specific geometry of the arrangement. Only cylindrical cavity resonators were used in each case. The calculation of the sound pressure course and other acoustic variables was performed over a frequency range from 20 Hz to 16000 Hz and the sound pressure level was plotted logarithmically in connection with the sound pressure.

Figure 4:
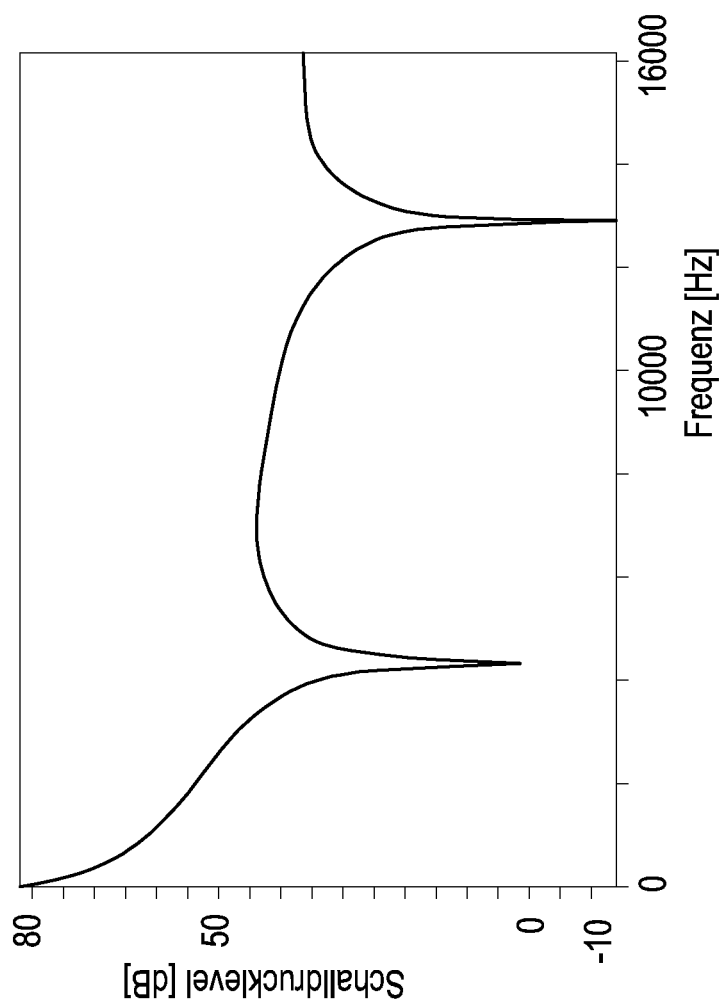
FIG. 4 is a representation of the sound pressure course determined for the acoustic filter member of FIG. 3.
Figure 3:
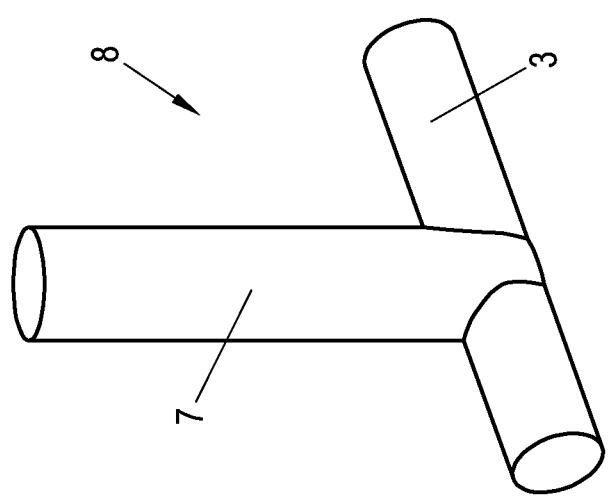
FIG. 3 is an exemplary representation of an acoustic filter member having a single cavity resonator.

The first acoustic filter member 8 examined is represented in FIG. 3; the corresponding sound pressure course is represented in FIG. 4. The diameter of the flow channel 3 is constantly 4 mm. The cylindrical cavity resonator 7 projecting vertically from flow channel 3 has a diameter of 5 mm and a length of 21 mm (measured from the axis of flow channel 3). With this configuration, an acoustic filter member having two notched negative value peaks of the sound pressure amplification was achieved, wherein the value peaks are at approx. 4100 Hz and at 12900 Hz.

Figure 6:
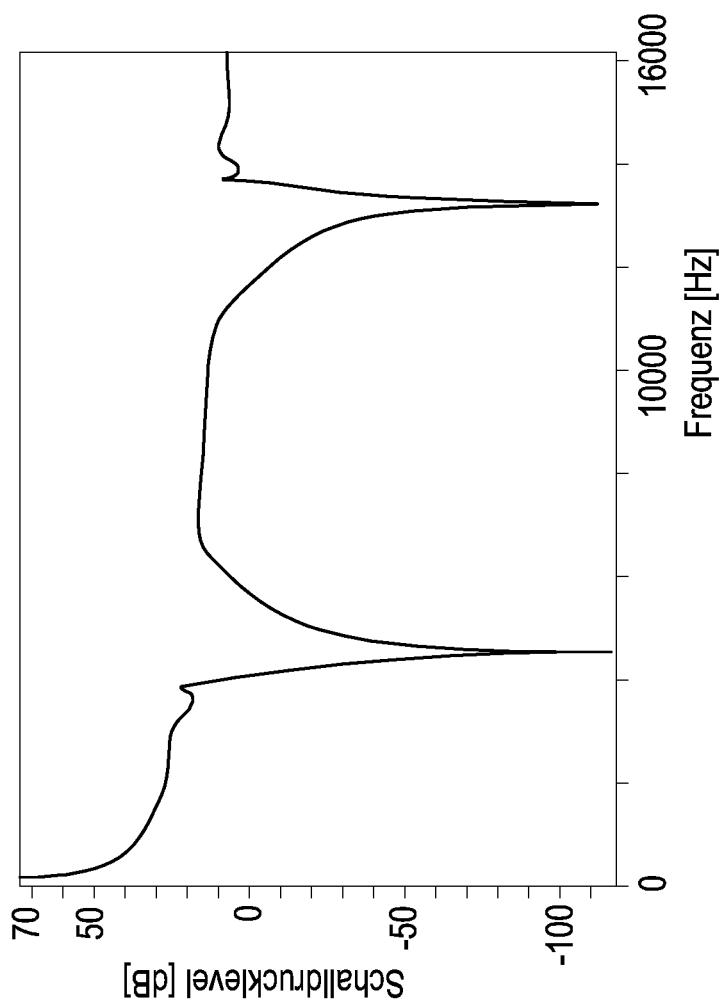
FIG. 6 is a representation of the sound pressure curve determined for the acoustic filter member of FIG. 5.
Figure 5:
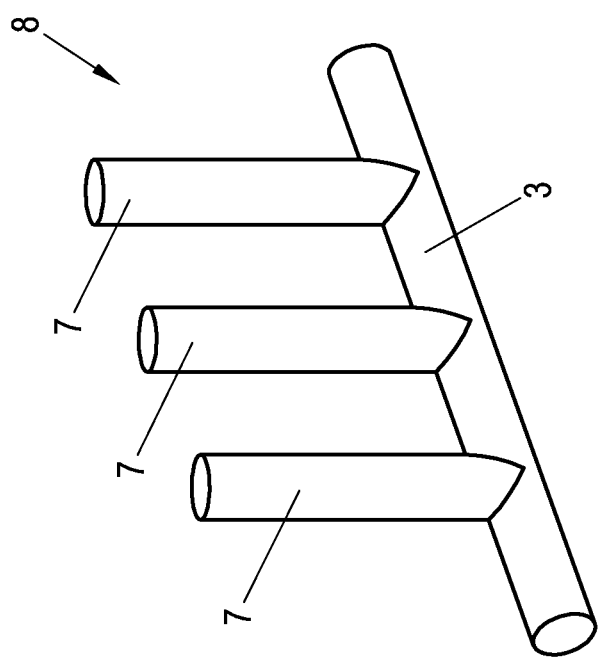
FIG. 5 is an exemplary representation of an acoustic filter member having three consecutively arranged one-sided cavity resonators of equal length.

The second examined acoustic filter member 8 is represented in FIG. 5; FIG. 6 shows the correspondingly determined sound pressure course. The diameter of the flow channel 3 is constantly 4 mm. The acoustic filter member 8 in FIG. 5 has three identical cylindrical cavity resonators 7 arranged on one side of the flow channel 3, each having a length of 21 mm. The distance between two successively arranged cavity resonators 7 is 10.5 mm and the diameter is 4 mm each. The sound pressure course of this configuration has two negative value peaks, which are arranged essentially at the same position as in the first fitter of FIG. 3, but the value peaks are noticeably wider and the attenuation is much more distinctive.

Figure 8:
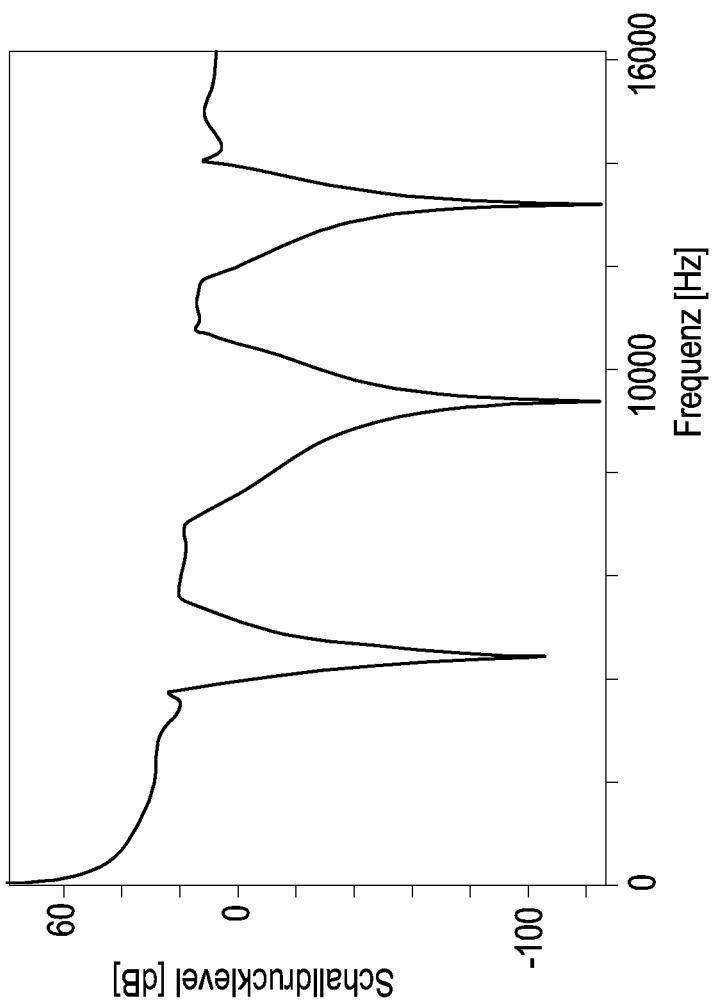
FIG. 8 is a representation of the sound pressure course determined for the acoustic filter member of FIG. 7.
Figure 7:
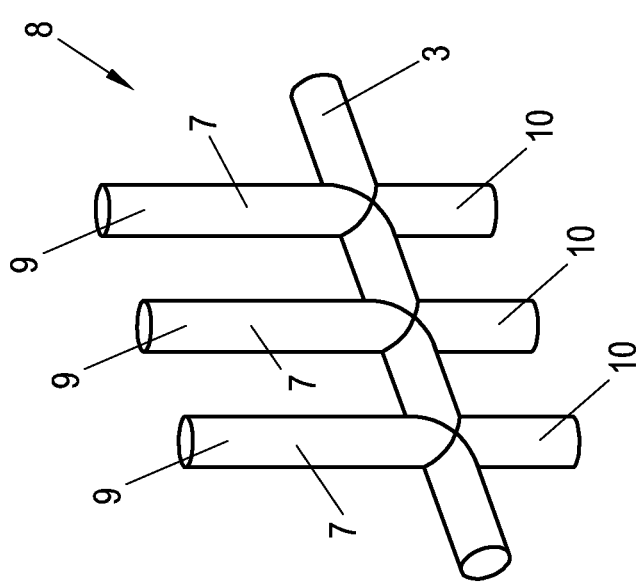
FIG. 7 is an exemplary representation of an acoustic filter member having three consecutively arranged double-sided cavity resonators of equal length.

The third examined acoustic filter member 8 is represented in FIG. 7; FIG. 8 shows the correspondingly determined sound pressure course. The diameter of the flow channel 3 is constantly 4 mm. The acoustic filter member 8 in FIG. 7 has three identical cylindrical cavity resonators 7 arranged in the flow channel 3. The cavity resonators extend on both sides of the flow channel 3, wherein a longer first neck or neck portion 9 is opposed by a shorter second neck or neck portion 10. The length of the first neck 9 is 21 mm each, the length of the second neck 10 is 10.5 mm each. The distance between two successively arranged cavity resonators 7 is 10.5 mm and the diameter are 4 mm each. Compared with the sound pressure course of the second examined acoustic filter member 8 shown in FIG. 6, the sound pressure course of this configuration has an additional negative value peak, which lies between the two (still present) previous value peaks at about 9200 Hz. The middle peak value is designed significantly wider than the two lateral value peaks.

Figure 10:
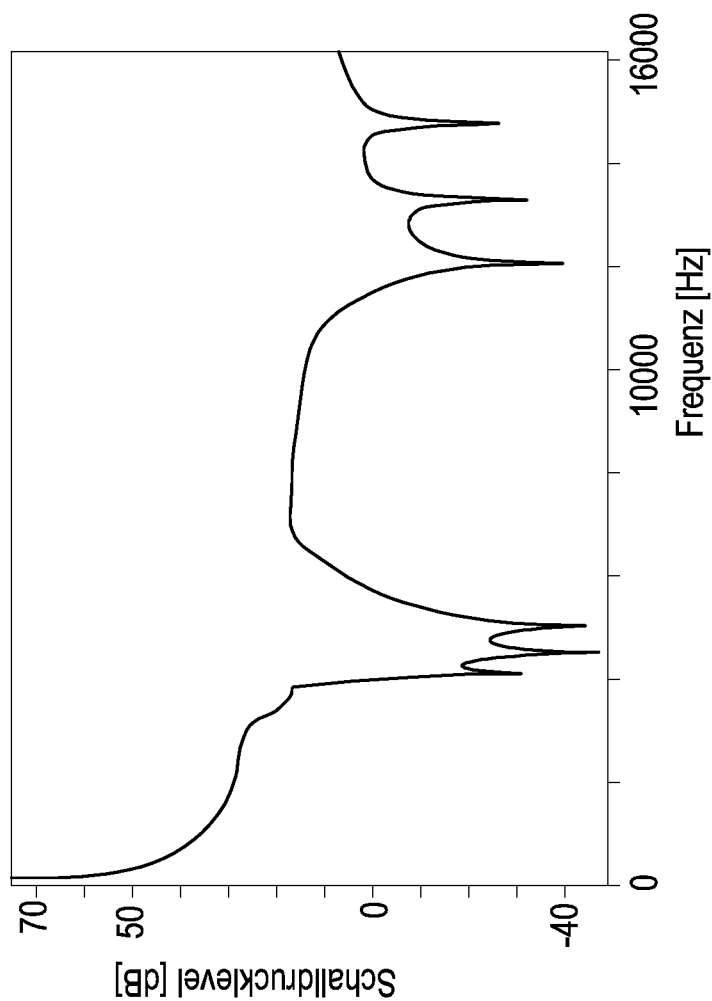
FIG. 10 is a representation of the sound pressure course determined for the acoustic filter member of FIG. 9.
Figure 9:
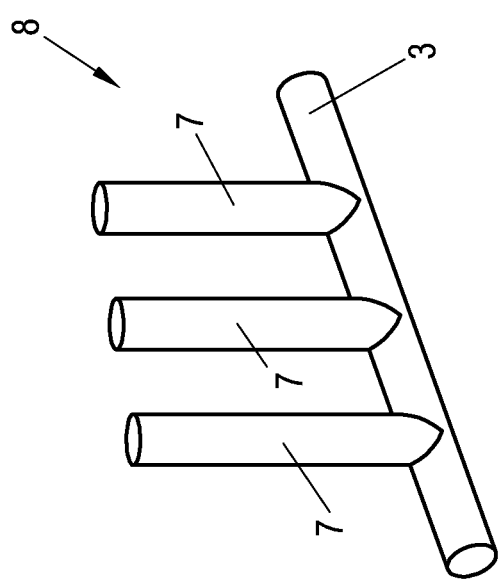
FIG. 9 is an exemplary representation of an acoustic filter member having three consecutively arranged one-sided cavity resonators of different length.

The fourth examined acoustic filter member 8 is represented in FIG. 9; FIG. 10 shows the correspondingly determined sound pressure course. The diameter of the flow channel 3 is constantly 4 mm. The acoustic filter member 8 in FIG. 9 has three cylindrical cavity resonators 7 arranged on one side of the flow channel 3, each of them having slightly different lengths of 23 mm, 21 mm and 19 mm. The distance between two successively arranged cavity resonators 7 is 10.5 mm and the diameter is 4 mm each. The sound pressure course of this configuration has two distinctive negative band areas, which extend between approx. 4000 Hz and approx. 5000 Hz, or between approx. 11900 Hz and approx. 15000 Hz.

Figure 12:
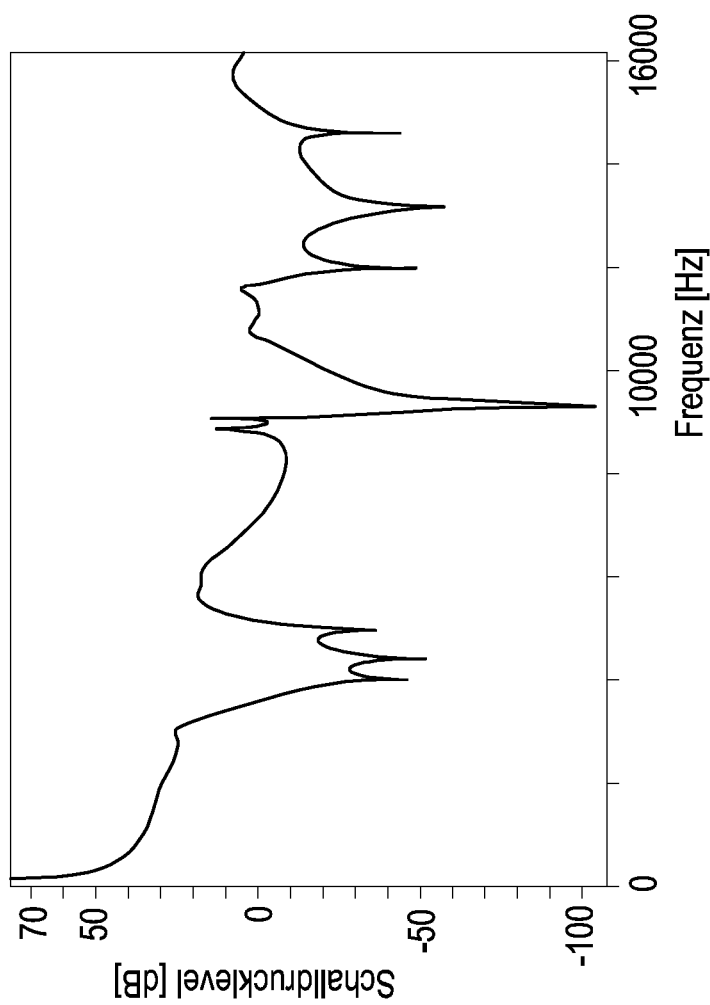
FIG. 12 is a representation of the sound pressure course determined for the acoustic filter member of FIG. 11.
Figure 11:
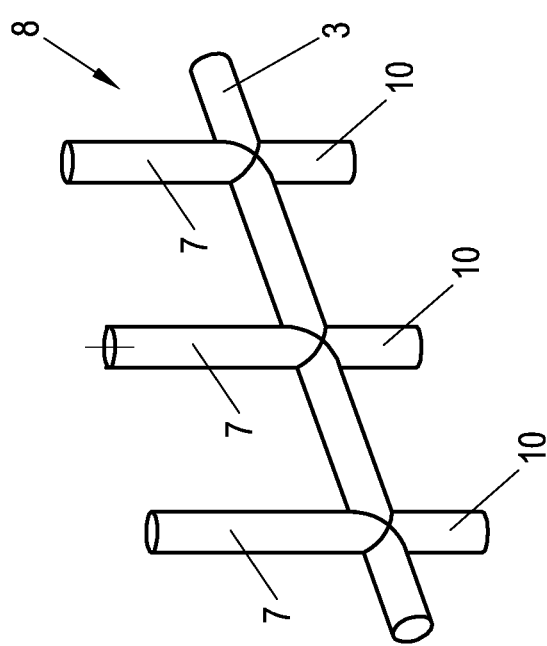
FIG. 11 is an exemplary representation of an acoustic filter member having three consecutively arranged double-sided cavity resonators of different length.

The fifth examined acoustic filter member 8 is shown in FIG. 11; FIG. 12 shows the correspondingly determined sound pressure course. Compared to the filter member shown in FIG. 9, on the one hand the distance between the cavity resonators 7 was increased to 21 mm each and every cavity resonator 7 was supplemented with a second, opposite neck or neck portion 10. The length of the second necks 10 is 10.5 mm each. The other parameters remained unchanged. This configuration also creates two distinctive negative band areas, which are located at essentially the same position as in the previous example in FIG. 10. Additionally, there is a very distinctive value peak at approx. 9200 Hz.

In addition to the 3D simulation described above, a calculation using a highly simplified two-dimensional model was repeated and the results were then compared. It turned out that the results of the 3D simulation and the 2D calculation are essentially equivalent in quality except for a scaling factor.

This illustrates a considerable advantage of the acoustic filter members 8, according to the invention, which are based on simple cylindrical cavity resonators 7, since a design of the filter properties can be carried out in a first step using simple 2D models. A found optimal configuration can then be checked using more complex modeling (e.g. in a simulation using a 3D model) or tested immediately in a practical implementation. (A measurement result of such a practical implementation is shown as an example in FIG. 2 and was discussed in the context of the description of this figure.)

To enable the person skilled in the art to put the invention into practice, the following conclusions were made by the inventors from the simulations and calculations:

The exact position of the value peaks essentially depends on the length of the resonator necks.

The depth (or height) of the value peaks depends on the number of resonators.

Wider, but not so deep indentations can be achieved by the use of a plurality of resonator necks having slightly varying lengths.

Additional slight displacements can be achieved by changes in the radii and diameters, as well as changes in the distances between the necks, but these parameters have a lesser effect.

REFERENCE NUMERALS

Measuring device 1
Measuring gas 2
Flow channel 3
Feed line 4
Measuring cell 5
Discharge line 6
Cavity resonator 7
Acoustic filter member 8
First neck portion 9
Second neck portion 10
Housing 11
Measuring gas inlet 12
Measuring gas outlet 13
Flow path 14
Attenuators 15
Vacuum pump 16
Helmholz resonator 17
Useful frequency 18

The invention claimed is:

1. A measuring device for determining a measured variable of a measuring gas by means of a photoacoustic method, wherein the measuring device comprises:
    a flow channel configured and arranged for measuring gas, and having at least one feed line;
    a photoacoustic measuring cell;
    a discharge line;
    at least one acoustic filter member configured and arranged to
        be tuned to a useful frequency of the photoacoustic measuring cell, and
        generate negative sound pressure amplification in a first frequency range including a fundamental frequency of the useful frequency; and
    wherein the at least one acoustic filter member includes at least one cavity resonator arranged on the flow channel at the at least one feed line and/or at the discharge line.

2. The measuring device according to claim 1, characterized in that an axis of the at least one cavity resonator is aligned normally to an axis of the flow channel.

3. The measuring device according to claim 1, characterized in that the at least one cavity resonator includes a first and second neck portions.

4. The measuring device of claim 3, wherein the first neck portion is arranged opposite the second neck portion.

5. The measuring device according to claim 1, characterized in that the at least one acoustic filter member includes a plurality of cavity resonators entering consecutively into the flow channel.

6. The measuring device according to claim 1, characterized in that the at least one acoustic filter member is configured and arranged to generate a negative sound pressure amplification in at least one second frequency range including a multiple of a fundamental frequency of the useful frequency.

7. The measuring device according to claim 1, characterized in that the at least one cavity resonator is cylindrical.

8. The measuring device according to claim 7, wherein the at least one acoustic filter member includes at least two cavity resonators, the at least two cavity resonators are cylindrical and each have a different length and/or a different diameter.

9. The measuring device according to claim 7, characterized in that the length of at least one cavity resonator of the at least two cavity resonators is adjustable.

10. The measuring device according to claim 1, further including a pressure-tight housing with the photoacoustic measuring cell positioned therein, and the pressure-tight housing is configured and arranged to be brought to negative pressure and/or vacuum.

11. A method for the suppression of sound interferences in a measuring device for determining a measured variable of a measuring gas by means of a photoacoustic method, the method including the steps of:
 conducting the measuring gas via a flow channel which runs through at least one feed line, a photoacoustic measuring cell and a discharge line,
 providing at least one acoustic filter member in the flow channel;
 adjusting the at least one acoustic filter member to a negative sound pressure amplification in a first frequency range including a fundamental frequency of a useful frequency; and
 arranging the at least one acoustic filter member at the at least one feed line and/or at the discharge line.

12. The method according to claim 11, wherein the step of adjusting the at least one acoustic filter member further includes adjusting the at least one acoustic filter member to a negative sound pressure amplification in at least one second frequency range including a multiple of the fundamental frequency of the useful frequency.

13. The method according to claim 11, wherein the step of adjusting the at least one acoustic filter member further includes a constructive defining and/or adjusting of at least one or a plurality of features of a cavity resonator including: shape, position, length, diameter, length of a cylindrical cavity resonator, and diameter of a cylindrical cavity resonator.

14. The method according to claim 11, further including the step of applying a negative pressure and/or vacuum to a housing in which the photoacoustic measuring cell is arranged.

* * * * *